(12) United States Patent
Kadereit et al.

(10) Patent No.: US 7,378,440 B2
(45) Date of Patent: May 27, 2008

(54) SUBSTITUTED BENZOYLUREIDO-O-BENZOYLAMIDES, PROCESS FOR THEIR PREPARATION AND THEIR USE

(75) Inventors: Dieter Kadereit, Kelkheim (DE); Elisabeth Defossa, Idstein (DE); Karl Schoenafinger, Alzenau (DE); Thomas Kalbunde, Frankfurt (DE); Andreas Herling, Bad Camberg (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 585 days.

(21) Appl. No.: 10/899,868

(22) Filed: Jul. 27, 2004

(65) Prior Publication Data
US 2005/0065142 A1    Mar. 24, 2005

Related U.S. Application Data

(60) Provisional application No. 60/527,731, filed on Dec. 8, 2003.

(30) Foreign Application Priority Data
Dec. 8, 2003    (DE) .............................. 103 35 092

(51) Int. Cl.
A61K 31/401    (2006.01)
A61K 31/403    (2006.01)
A61K 31/445    (2006.01)
A61K 31/397    (2006.01)
C07D 207/09    (2006.01)
C07D 209/12    (2006.01)
C07D 205/04    (2006.01)
C07D 211/06    (2006.01)

(52) U.S. Cl. ...................... 514/423; 514/412; 514/330; 514/210.17; 546/226; 548/452; 548/533; 548/953

(58) Field of Classification Search ................. 546/226
See application file for complete search history.

(56) References Cited

U.S. PATENT DOCUMENTS

| | | | |
|---|---|---|---|
| 2,149,335 A * | 3/1939 | Dahlen et al. ............... 544/234 |
| 5,190,923 A | 3/1993 | Vincent et al. |
| 6,121,311 A | 9/2000 | Matsubara et al. |
| 6,221,633 B1 | 4/2001 | Ertl et al. |
| 6,221,897 B1 | 4/2001 | Frick et al. |
| 6,245,744 B1 | 6/2001 | Frick et al. |
| 6,342,512 B1 | 1/2002 | Kirsch et al. |
| 6,380,357 B2 | 4/2002 | Hermeling et al. |
| 6,506,778 B2 | 1/2003 | Defossa et al. |
| 6,624,185 B2 | 9/2003 | Glombik et al. |
| 6,812,250 B2 | 11/2004 | Defossa et al. |
| 6,884,812 B2 | 4/2005 | Glombik et al. |
| 7,179,941 B2 * | 2/2007 | Defossa et al. ................ 564/44 |

FOREIGN PATENT DOCUMENTS

| EP | 136745 A2 * | 4/1985 |
|---|---|---|
| EP | 545441 A1 * | 6/1993 |
| WO | WO 91/11457 | 8/1991 |
| WO | WO 97/26265 | 7/1997 |
| WO | WO 97/41097 | 11/1997 |
| WO | WO 99/03861 | 1/1999 |
| WO | WO 99/15525 | 4/1999 |
| WO | WO 00/34331 | 6/2000 |
| WO | WO 00/34332 | 6/2000 |
| WO | WO 00/40569 | 7/2000 |
| WO | WO 00/63208 | 10/2000 |
| WO | WO 00/64876 | 11/2000 |
| WO | WO 00/64888 | 11/2000 |
| WO | WO 00/66585 | 11/2000 |
| WO | WO 00/71549 | 11/2000 |
| WO | WO 00/78312 | 12/2000 |
| WO | WO 01/04156 | 1/2001 |
| WO | WO 01/09111 | 2/2001 |
| WO | WO 01/83451 | 11/2001 |
| WO | WO 01/85695 | 11/2001 |
| WO | WO 01/91752 | 12/2001 |
| WO | WO 01/94300 | 12/2001 |
| WO | WO 02/096864 | 12/2002 |
| WO | WO 03/104188 | 12/2003 |

OTHER PUBLICATIONS

Dorwald F. A. Side Reactions in Organic Synthesis, 2005, Wiley: VCH, Weinheim p. IX of Preface & p. 41.*
Gary M. Coppola, "The Chemistry of Isatoic Anhydride" Synthesis 1980, 505-536.*
Dudash et. al. "Synthesis and evaluation of 3-anilino-quinoxalinones as glycogen phosphorylase inhibitors" Bioorganic & Medicinal Chemistry Letters 2005, 15, 4790-4793.*

(Continued)

*Primary Examiner*—Rita Desai
*Assistant Examiner*—David K O'Dell
(74) *Attorney, Agent, or Firm*—Barbara E. Kurys

(57) ABSTRACT

The invention relates to substituted benzoylureido-o-benzoylamides and to their physiologically tolerated salts and physiologically functional derivatives.

The invention relates to compounds of the formula I

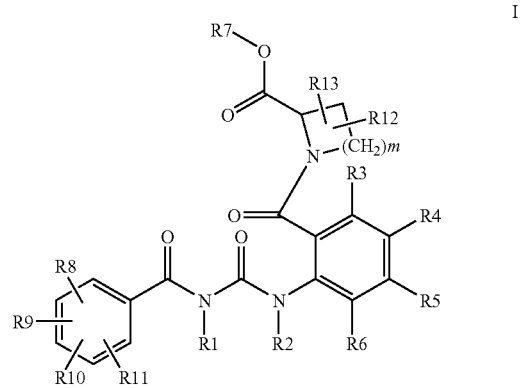

in which the radicals have the stated meanings, and to the physiologically tolerated salts thereof. The compounds are suitable for example as medicaments for the prevention and treatment of type 2 diabetes.

2 Claims, No Drawings

OTHER PUBLICATIONS

Asakawa, A., et al., Cocaine-Amphetamine-Regulated Transcript Influences Energy Metabolism, Anxiety and Gastric Emptying in Mice, Hormone and Metabolic Research, 2001, vol. 33(9), pp. 554-558.

Drueckes, P., et al., Photometric Microtiter Assay of Inorganic Phosphate in the Presence of Acid-Labile Organic Phosphates, Anal. Biochem, 1995, vol. 230(1), pp. 173-177.

Lee, D.W., et al., Leptin agonists as a potential approach to the treatment of obestiy, Drugs of the Future, 2001, vol. 26(9), pp. 873-881.

Okada, H., et. al., Synthesis and Antitumor Activities of Prodrugs of Benzoylphenylureas, Chem. Pharm. Bull., 1994, vol. 42(1), pp. 57-61.

Salvador, J., et. al., Perspectives in the therapeutic use of leptin, Expert Opinion on Pharmacotherapy 2001, 2(10), 1615-1622.

Tyle, P., Iontophoretic Devices for Drug Delivery, Pharmaceutical Research, vol. 3, No. 6, 1986 pp. 318-326.

Zunft, H., et. al., Carob Pulp Preparation for Treatment of Hypercholesterolemia, Advances in Therapy, 2001, vol. 18(5), pp. 230-236.

* cited by examiner

SUBSTITUTED BENZOYLUREIDO-O-BENZOYLAMIDES, PROCESS FOR THEIR PREPARATION AND THEIR USE

The invention relates to substituted benzoylureido-o-benzoylamides and to their physiologically tolerated salts and physiologically functional derivatives.

Compounds of similar structure and their use for the treatment of cocaine dependence have already been described in the prior art (U.S. Pat. No. 6,121,311).

The invention was based on the object of providing compounds with which prevention and treatment of diabetes mellitus is possible. It was intended that the compounds display for this purpose in particular a blood glucose-lowering effect which can be utilized therapeutically.

The invention therefore relates to compounds of the formula I

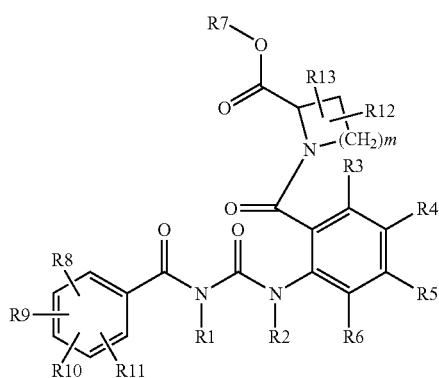

wherein

R1, R2 are each, independently of one another, H or ($C_1$-$C_6$)-alkyl,
  wherein said ($C_1$-$C_6$)-alkyl is optionally substituted by OH, O—($C_1$-$C_4$)-alkyl, $NH_2$, NH($C_1$-$C_4$)-alkyl, N[($C_1$-$C_6$)-alkyl]$_2$, or O—($C_1$-$C_6$)-alkyl, CO—($C_1$-$C_6$)-alkyl, COO—($C_1$-$C_6$)-alkyl, ($C_1$-$C_6$)-alkylene-COOH or ($C_1$-$C_6$)-alkylene-COO—($C_1$-$C_6$)-alkyl;

R3, R4, R5, R6 are each, independently of one another, H, F, Cl, Br, $NO_2$, CN, O—R14, O-phenyl, S—R14, COOR14, N(R15)(R16), ($C_1$-$C_6$)-alkyl, ($C_2$-$C_6$)-alkenyl, ($C_2$-$C_6$)-alkynyl, ($C_3$-$C_7$)-cycloalkyl, ($C_3$-$C_7$)-cycloalkyl-($C_1$-$C_4$)-alkylene or O—($C_1$-$C_5$)-alkylene-COOR14,
  wherein said ($C_1$-$C_6$)-alkyl, ($C_2$-$C_6$)-alkenyl, ($C_2$-$C_6$)-alkynyl, ($C_3$-$C_7$)-cycloalkyl, ($C_3$-$C_7$)-cycloalkyl-($C_1$-$C_4$)-alkylene and O—($C_1$-$C_5$)-alkylene-COOR14 are optionally substituted one or more times by F, Cl, Br, OR14, COOR14 or N(R15)(R16);

R7 is H, ($C_1$-$C_6$)-alkyl, ($C_2$-$C_6$)-alkenyl or ($C_1$-$C_6$)-alkylene-OOC—($C_1$-$C_6$)-alkyl,
  wherein said ($C_1$-$C_6$)-alkyl, ($C_2$-$C_6$)-alkenyl and ($C_1$-$C_6$)-alkylene-OOC—($C_1$-$C_6$)-alkyl are optionally substituted one or more times by F, Cl or OR14;

R8, R9, R10, R11 are each, independently of one another, H, F, Cl, Br, OH, $NO_2$, CN, O—($C_1$-$C_6$)-alkyl, O—($C_2$-$C_6$)-alkenyl, O—($C_2$-$C_6$)-alkynyl, O—$SO_2$—($C_1$-$C_4$)-alkyl, ($C_1$-$C_6$)-alkyl, ($C_2$-$C_6$)-alkenyl or ($C_2$-$C_6$)-alkynyl,
  wherein said O—($C_1$-$C_6$)-alkyl, O—($C_2$-$C_6$)-alkenyl, O—($C_2$-$C_6$)-alkynyl, O—$SO_2$—($C_1$-$C_4$)-alkyl, ($C_1$-$C_6$)-alkyl, ($C_2$-$C_6$)-alkenyl and ($C_2$-$C_6$)-alkynyl are optionally substituted one or more times by F, Cl or Br;

R12, R13 are each, independently of one another, H, OH, oxo, F, ($C_1$-$C_6$)-alkyl, ($C_6$-$C_{10}$)-aryl, ($C_1$-$C_6$)-alkylene-($C_6$-$C_{10}$)-aryl, O—($C_1$-$C_6$)-alkyl, O—($C_2$-$C_6$)-alkenyl or O—($C_2$-$C_6$)-alkynyl,
  wherein said ($C_1$-$C_6$)-alkyl, ($C_6$-$C_{10}$)-aryl, ($C_1$-$C_6$)-alkylene-($C_6$-$C_{10}$)-aryl, O—($C_1$-$C_6$)-alkyl, O—($C_2$-$C_6$)-alkenyl and O—($C_2$-$C_6$)-alkynyl radicals are optionally substituted one or more times by F, Cl or Br; or R12 and R13 form together, with the carbon atom or the carbon atoms to which they are bonded, a 3-, 4-, 5-, 6- or 7-membered, saturated or unsaturated ring which optionally comprises up to 2 further heteroatoms from the group consisting of N, O or S,
  wherein said ring is optionally substituted up to three times by F, Cl, Br, OH, oxo, N(R17)(R18) or ($C_1$-$C_4$)-alkyl;

R14 is H, ($C_1$-$C_8$)-alkyl, ($C_2$-$C_8$)-alkenyl or ($C_2$-$C_8$)-alkynyl, wherein said ($C_1$-$C_8$)-alkyl, ($C_2$-$C_8$)-alkenyl and ($C_2$-$C_8$)-alkynyl are optionally substituted one or more times by F, Cl, Br, OH or O—($C_1$-$C_4$)-alkyl;

R15, R16 are each, independently of one another, H, ($C_1$-$C_8$)-alkyl, ($C_2$-$C_8$)-alkenyl, ($C_2$-$C_8$)-alkynyl, ($C_3$-$C_7$)-cycloalkyl, ($C_3$-$C_7$)-cycloalkyl-($C_1$-$C_4$)-alkylene, COO—($C_1$-$C_4$)-alkyl, COO—($C_2$-$C_4$)-alkenyl, phenyl or $SO_2$-phenyl,
  wherein said phenyl and $SO_2$-phenyl are optionally substituted up to twice by F, Cl, CN, OH, ($C_1$-$C_6$)-alkyl, O—($C_1$-$C_6$)-alkyl, $CF_3$, $OCF_3$, COOH, COO—($C_1$-$C_6$)-alkyl or $CONH_2$; or R15 and R16 form together, with the nitrogen atom to which they are bonded, a 3-, 4-, 5-, 6- or 7- membered, saturated heterocyclic ring optionally comprising up to 2 further heteroatoms from the group consisting of N, O or S,
  wherein said heterocyclic ring is optionally substituted up to three times by F, Cl, Br, OH, oxo, N(R17)(R18) or ($C_1$-$C_4$)-alkyl;

R17, R18 are each, independently of one another, H, ($C_1$-$C_8$)-alkyl, ($C_2$-$C_8$)-alkenyl, ($C_2$-$C_8$)-alkynyl, ($C_3$-$C_7$)-cycloalkyl, ($C_3$-$C_7$)-cycloalkyl-($C_1$-$C_4$)-alkylene, COO—($C_1$-$C_4$)-alkyl, COO—($C_2$-$C_4$)-alkenyl, phenyl or $SO_2$-phenyl,
  wherein said phenyl and $SO_2$-phenyl are optionally substituted up to twice by F, Cl, CN, OH, ($C_1$-$C_6$)-alkyl, O—($C_1$-$C_6$)-alkyl, $CF_3$, $OCF_3$, COOH, COO—($C_1$-$C_6$)-alkyl or $CONH_2$;

m is 1, 2, 3 or 4;

with the proviso that when m is 2, R8 and R9 cannot both be hydrogen, and pharmaceutically acceptable salts thereof.

Preference is given to compounds of the formula I in which one or more radicals have the following meaning:

R1,R2 are H;

R3, R4, R5, R6 are each, independently of one another, H, F, Cl, Br, $NO_2$, CN, O—R14, O-phenyl, S—R14, COOR14, N(R15)(R16), ($C_1$-$C_6$)-alkyl, ($C_2$-$C_6$)-alkenyl, ($C_2$-$C_6$)-alkynyl, ($C_3$-$C_7$)-cycloalkyl, ($C_3$-$C_7$)-cycloalkyl-($C_1$-$C_4$)-alkylene or O—($C_1$-$C_5$)-alkylene-COOR14,
  wherein said ($C_1$-$C_6$)-alkyl, ($C_2$-$C_6$)-alkenyl, ($C_2$-$C_6$)-alkynyl, ($C_3$-$C_7$)-cycloalkyl, ($C_3$-$C_7$)-cycloalkyl-($C_1$-$C_4$)-alkylene and O—($C_1$-$C_5$)-alkylene-COOR14 are optionally substituted one or more times by F, Cl, Br, OR14, COOR14 or N(R15)(R16);

R7 is H, ($C_1$-$C_6$)-alkyl, ($C_2$-$C_6$)-alkenyl or ($C_1$-$C_6$)-alkylene-OOC—($C_1$-$C_6$)-alkyl, wherein said $(C_1-C_6)$-alkyl, $(C_2-C_6)$-alkenyl and $(C_1-C_6)$-alkylene-OOC—$(C_1-C_6)$-alkyl are optionally substituted one or more times by F, Cl or OR14;

R8, R9, R10, R11 are each, independently of one another, H, F, Cl, Br, OH, $NO_2$, CN or O—$(C_1-C_6)$-alkyl,
  wherein said O—$(C_1-C_6)$-alkyl is optionally substituted one or more times by F, Cl or Br;

R12, R13 are each, independently of one another, H, OH, oxo, F, $(C_1-C_6)$-alkyl, $(C_6-C_{10})$-aryl, $(C_1-C_6)$-alkylene-$(C_6-C_{10})$-aryl, O—$(C_1-C_6)$-alkyl, O—$(C_2-C_6)$-alkenyl or O—$(C_2-C_6)$-alkynyl,
  wherein said $(C_1-C_6)$-alkyl, $(C_6-C_{10})$-aryl, $(C_1-C_6)$-alkylene-$(C_6-C_{10})$-aryl, O—$(C_1-C_6)$-alkyl, O—$(C_2-C_6)$-alkenyl and O—$(C_2-C_6)$-alkynyl radicals are optionally substituted one or more times by F, Cl or Br; or R12 and R13 form together, with the carbon atom or the carbon atoms to which are bonded, a 3-, 4-, 5-, 6- or 7-membered, saturated or unsaturated ring which optionally comprises up to 2 further heteroatoms from the group consisting of N, O or S,
  wherein said ring is optionally substituted up to three times by F, Cl, Br, OH, oxo, N(R17)(R18) or $(C_1-C_4)$-alkyl;

R14 is H, $(C_1-C_8)$-alkyl, $(C_2-C_8)$-alkenyl or $(C_2-C_8)$-alkynyl,
  wherein said $(C_1-C_8)$-alkyl, $(C_2-C_8)$-alkenyl and $(C_2-C_8)$-alkynyl is optionally substituted one or more times by F, Cl, Br, OH or O—$(C_1-C_4)$-alkyl;

R15, R16 are each, independently of one another, H, $(C_1-C_8)$-alkyl, $(C_2-C_8)$-alkenyl, $(C_2-C_8)$-alkynyl, $(C_3-C_7)$-cycloalkyl, $(C_3-C_7)$-cycloalkyl-$(C_1-C_4)$-alkylene, COO—$(C_1-C_4)$-alkyl, COO—$(C_2-C_4)$-alkenyl, phenyl or $SO_2$-phenyl,
  wherein said phenyl and $SO_2$-phenyl are optionally substituted up to twice by F, Cl, CN, OH, $(C_1-C_6)$-alkyl, O—$(C_1-C_6)$-alkyl, $CF_3$, $OCF_3$, COOH, COO$(C_1-C_6)$-alkyl or $CONH_2$; or R15 and R16 form together, with the nitrogen atom to which they are bonded, a 3-, 4-, 5-, 6- or 7-membered, saturated heterocyclic ring optionally comprising up to 2 further heteroatoms from the group of N, O or S,
  wherein said heterocyclic ring is optionally substituted up to three times by F, Cl, Br, OH, oxo, N(R17)(R18) or $(C_1-C_4)$-alkyl;

R17, R18 are each, independently of one another, H or $(C_1-C_8)$-alkyl;

m is 1, 2, 3 or 4;

with the proviso that when m is 2, R8 and R9 cannot both be hydrogen, and pharmaceutically acceptable salts thereof.

Particular preference is given to compounds of the formula I in which one or more radicals have the following meaning:
R1, R2 are H;
R3, R4, R5, R6 are each, independently of one another, H, F, Cl, $CF_3$ or COOR14;
R7 is H or $(C_1-C_6)$-alkyl;
R8, R9 are each, independently of one another, F or Cl;
R10, R11 are each, independently of one another, H, F, or Cl;
R12, R13 are each, independently of one another, H or F; or
R12 and R13 form together, with the carbon atom or the carbon atoms to which they are bonded, a 5- or 6-membered, saturated ring;
R14 is H or $(C_1-C_4)$-alkyl;
m is 1, 2 or 3;

and pharmaceutically acceptable salts thereof.

Very particular preference is given to compounds of the formula I in which one or more radicals have the following meaning:
R1, R2 are H;
R3, R4, R5, R6 are H;
R7 is H or $(C_1-C_6)$-alkyl;
R8, R9 are each, independently of one another, F or Cl;
R10, R11 are each, independently of one another, H, F, or Cl;
R12, R13 are each, independently of one another, H or F; or
R12 and R13 form together, with the carbon atom or the carbon atoms to which they are bonded, a 5- or 6-membered, saturated ring;
m is 1, 2 or 3;

and pharmaceutically acceptable salts thereof.

The invention relates to compounds of the formula I in the form of their racemates, racemic mixtures and pure enantiomers and to their diastereomers and mixtures thereof.

If radicals or substituents may occur more than once in the compounds of the formula I, they may all, independently of one another, have the stated meaning and be identical or different.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), trometamol(2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

An alkyl radical means a straight-chain or branched hydrocarbon chain having one or more carbons, such as, for example, methyl, ethyl, isopropyl, tert-butyl, hexyl. The alkyl radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2SO_2NH$($C_1$-$C_6$)-alkyl, $SO_2N$[($C_1$-$C_6$)-alkyl]2, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$,, $SO_2$—N(($CH_2$)$_n$-(heterocycle)$_2$, where n can be 0-6, and the aryl radical or heterocylic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$;

C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl-CO—($C_1$-$C_6$)-alkyl, N($C_1$-$C_6$)-alkyl-COO—($C_1$-$C_6$)-alkyl, N($C_1$-$C_6$)-alkyl-CO-aryl, N($C_1$-$C_6$)-alkyl-CO-heterocycle, N($C_1$-$C_6$)-alkyl-COO-aryl, N($C_1$-$C_6$)-alkyl-COO-heterocycle, N($C_1$-$C_6$)-alkyl-CO—NH—($C_1$-$C_6$)-alkyl), N($C_1$-$C_6$)-alkyl-CO—NH-aryl, N($C_1$-$C_6$)-alkyl-CO—NH-heterocycle, N(($C_1$-$C_6$)-alkyl)-CO—N-($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

An alkenyl radical means a straight-chain or branched hydrocarbon chain having two or more carbons and one or more double bonds, such as, for example, vinyl, allyl, pentenyl.

The alkenyl radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH ($C_1$-$C_6$)alkyl, CON[($C_1$-$C_6$)alkyl]$_2$, cycloalkyl, ($C_1$-$C_{10}$)-alkyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2NH$($C_1$-$C_6$)-alkyl, $SO_2N$[($C_1$-$C_6$)-alkyl]$_2$, alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$,, $SO_2$—N(($CH_2$)$_n$-(heterocycle)$_2$ where n may be 0-6 and the aryl radical or the heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$;

C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl-CO—($C_1$-$C_6$)-alkyl, N($C_1$-$C_6$)-alkyl-COO—($C_1$-$C_6$)-alkyl, N($C_1$-$C_6$)-alkyl-CO-aryl, N($C_1$-$C_6$)-alkyl-CO-heterocycle, N($C_1$-$C_6$)-alkyl-COO-aryl, N($C_1$-$C_6$)-alkyl-COO-heterocycle, N($C_1$-$C_6$)-alkyl-CO—NH—($C_1$-$C_6$)-alkyl), N($C_1$-$C_6$)-alkyl-CO—NH-aryl, N($C_1$-$C_6$)-alkyl-CO—NH-heterocycle, N(($C_1$-$C_6$)-alkyl)-CO—N-($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocyle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-Alkyl)-Aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

An alkynyl radical means a straight-chain or branched hydrocarbon chain having two or more carbons and one or more triple bonds, such as, for example, ethynyl, propynyl, hexynyl.

The alkynyl radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH ($C_1$-$C_6$)alkyl, CON[($C_1$-$C_6$)alkyl]$_2$, cycloalkyl, ($C_2$-$C_6$)-alkenyl, ($C_1$-$C_{10}$)-alkyl, O—($C_1$-$C_6$)-alkyl O—CO—($C_1$-$C_6$)-alkyl, O—CO—($C_1$-$C_6$)-Aryl, O—CO—($C_1$-$C_6$)-heterocycle;

$PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$-($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6 and the aryl radical or the heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$;

C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl-CO—($C_1$-$C_6$)-alkyl, N($C_1$-$C_6$)-alkyl-COO—($C_1$-$C_6$)-alkyl, N($C_1$-$C_6$)-alkyl-CO-aryl, N($C_1$-$C_6$)-alkyl-CO-heterocycle, N($C_1$-$C_6$)-alkyl-COO-aryl, N($C_1$-$C_6$)-alkyl-COO-heterocycle, N($C_1$-$C_6$)-alkyl-CO—NH—($C_1$-$C_6$)-alkyl), N($C_1$-$C_6$)-alkyl-CO—NH-aryl, N($C_1$-$C_6$)-alkyl-CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-Alkyl)-Aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

An aryl radical means a phenyl, naphthyl, biphenyl, tetrahydronaphthyl, alpha- or beta-tetralon-, indanyl- or indan-1-on-yl radical.

The aryl radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_1$-$C_{10}$)-alkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-Aryl, O—CO—($C_1$-$C_6$)-heterocycle; $PO_3H_2$, $SO_3H$, $SO_2$—$NH_2SO_2$NH($C_1$-$C_6$)-alkyl, $SO_2$N[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$-($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$,, $SO_2$—N(($CH_2$)$_n$-(heterocycle)$_2$ where n may be 0-6 and the aryl radical or the heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$;

C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl-CO—($C_1$-$C_6$)-alkyl, N($C_1$-$C_6$)-alkyl-COO—($C_1$-$C_6$)-alkyl, N($C_1$-$C_6$)-alkyl-CO-aryl, N($C_1$-$C_6$)-alkyl-CO-heterocycle, N($C_1$-$C_6$)-alkyl-COO-aryl, N($C_1$-$C_6$)-alkyl-COO-heterocycle, N($C_1$-$C_6$)-alkyl-CO—NH—($C_1$-$C_6$)-alkyl), N($C_1$-$C_6$)-alkyl-CO—NH-aryl, N($C_1$-$C_6$)-alkyl-CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-Alkyl)-Aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

A cycloalkyl radical means a ring system which comprises one or more rings and which is unsaturated or partially unsaturated (with one or two double bonds) and which is composed exclusively of carbon atoms, for example, cyclopropyl, cyclopentyl, cyclopentenyl, cyclohexyl or adamantyl.

The cycloalkyl radicals radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_1$-$C_{10}$)-alkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-Aryl, O—CO—($C_1$-$C_6$)-heterocycle; $PO_3H_2$, $SO_3H$, $SO_2$—$NH_2$, $SO_2$NH($C_1$-$C_6$)-alkyl, $SO_2$N[($C_1$-$C_6$)-alkyl]$_2$, alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$,, $SO_2$—N(($CH_2$)$_n$-(heterocycle)$_2$ where n may be 0-6 and the aryl radical or the heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$;

C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl-CO—($C_1$-$C_6$)-alkyl, N($C_1$-$C_6$)-alkyl-COO—($C_1$-$C_6$)-alkyl, N($C_1$-$C_6$)-alkyl-CO-aryl, N($C_1$-$C_6$)-alkyl-CO-heterocycle, N($C_1$-$C_6$)-alkyl-COO-aryl, N($C_1$-$C_6$)-alkyl-COO-heterocycle, N($C_1$-$C_6$)-alkyl-CO—NH—($C_1$-$C_6$)-alkyl), N($C_1$-$C_6$)-alkyl-CO—NH-aryl, N(C i-$C_6$)-alkyl-CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-C6)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-Alkyl)-Aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—(CH$_2$)$_n$-aryl, O—(CH$_2$)$_n$-heterocycle, where n may be 0-6, where the aryl radical or heterocyclic radical may be substituted one to 3 times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl, CONH$_2$.

Heterocycle or heterocyclic radical means rings or ring systems which, apart from carbon, also comprise heteroatoms such as, for example, nitrogen, oxygen or sulfur. Ring systems in which the heterocycle or heterocyclic radical is fused to benzene nuclei are also included in this definition.

Suitable "heterocyclic rings" or "heterocyclic radicals" are acridinyl, azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H, 6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl.

Pyridyl stands both for 2-, 3- and 4-pyridyl. Thienyl stands both for 2- and 3-thienyl. Furyl stands both for 2- and 3-furyl.

Also included are the corresponding N-oxides of the compounds, that is to say, for example, 1-oxy-2-, 3- or 4-pyridyl.

Also included are derivatives of these heterocycles which are benzo-fused one or more times.

The heterocyclic rings or heterocyclic radicals may be substituted one or more times by suitable groups such as, for example: F, Cl, Br, I, CF$_3$, NO$_2$, N$_3$, CN, COOH, COO(C$_1$-C$_6$)alkyl, CONH$_2$, CONH(C$_1$-C$_6$)alkyl, CON[(C$_1$-C$_6$)alkyl]$_2$, cycloalkyl, (C$_1$-C$_{10}$)-alkyl, (C$_2$-C$_6$)-alkenyl, (C$_2$-C$_6$)-alkynyl, O—(C$_1$-C$_6$)-alkyl O—CO—(C$_1$-C$_6$)-alkyl, O—CO—(C$_1$-C$_6$)-aryl, O—CO—(C$_1$-C$_6$)-heterocycle; PO$_3$H$_2$, SO$_3$H, SO$_2$—NH$_2$SO$_2$NH(C$_1$-C$_6$)-alkyl, SO$_2$N[(C$_1$-C$_6$)-alkyl]$_2$, S—(C$_1$-C$_6$)-alkyl, S—(CH$_2$)$_n$-aryl, S—(CH$_2$)$_n$-heterocycle, SO—(C$_1$-C$_6$)-alkyl, SO—(CH$_2$)$_n$-aryl, SO—(CH$_2$)$_n$-heterocycle, SO$_2$—(C$_1$-C$_6$)-alkyl, SO$_2$—(CH$_2$)$_n$-aryl, SO$_2$—(CH$_2$)$_n$-heterocycle, SO$_2$—NH(CH$_2$)$_n$-aryl, SO$_2$—NH(CH$_2$)$_n$-heterocycle, SO$_2$—N(C$_1$-C$_6$)-alkyl)(CH$_2$)$_n$-aryl, SO$_2$—N(C$_1$-C$_6$)-alkyl)(CH$_2$)$_n$-heterocycle, SO$_2$—N((CH$_2$)$_n$-aryl)$_2$, SO$_2$—N((CH$_2$)$_n$-(heterocycle)$_2$, where n can be 0-6, and the aryl radical or heterocylic radical may be substituted up to twice by F, Cl, Br, OH, CF$_3$, NO$_2$, CN, OCF$_3$, O—(C$_1$-C$_6$)-alkyl, (C$_1$-C$_6$)-alkyl, NH$_2$; C(NH)(NH$_2$), NH$_2$, NH—(C$_1$-C$_6$)-alkyl, N((C$_1$-C$_6$)-alkyl)$_2$, NH(C$_1$-C$_7$)-acyl, NH—CO—(C$_1$-C$_6$)-alkyl, NH—COO—(C$_1$-C$_6$)-alkyl, NH—CO-aryl, NH—CO-heterocycle, NH—COO-aryl, NH—COO-heterocycle, NH—CO—NH—(C$_1$-C$_6$)-alkyl, NH—CO—NH-aryl, NH—CO—NH-heterocycle, N(C$_1$-C$_6$)-alkyl-CO—(C$_1$-C$_6$)-alkyl, N(C$_1$-C$_6$)-alkyl-COO—(C$_1$-C$_6$)-alkyl, N(C$_1$-C$_6$)-alkyl-CO-aryl, N(C$_1$-C$_6$)-alkyl-CO-heterocycle, N(C$_1$-C$_6$)-alkyl-COO-aryl, N(C$_1$-C6)-alkyl-COO-heterocycle, N(C$_1$-C$_6$)-alkyl-CO—NH—(C$_1$-C$_6$)-alkyl), N(C$_1$-C$_6$)-alkyl-CO—NH-aryl, N(C$_1$-C$_6$)-alkyl-CO—NH-heterocycle, N((C$_1$-C$_6$)-alkyl)-CO—N—(C$_1$-C$_6$)-alkyl)$_2$, N((C$_1$-C$_6$)-alkyl)-CO—N((C$_1$-C$_6$)-alkyl)-aryl, N((C$_1$-C$_6$)-alkyl)-CO—N((C$_1$-C$_6$)-alkyl)-heterocycle, N((C$_1$-C$_6$)-alkyl)-CO—N-(aryl)$_2$, N((C$_1$-C$_6$)-alkyl)-CO—N-(heterocycle)$_2$, N(aryl)-CO—(C$_1$-C$_6$)-alkyl, N(heterocycle)-CO—(C$_1$-C$_6$)-alkyl, N(aryl)-COO—(C$_1$-C$_6$)-alkyl, N(heterocycle)-COO—(C$_1$-C$_6$)-alkyl, N(aryl)-CO-aryl, N(heterocycle)-CO-aryl, N(aryl)-COO-aryl, N(heterocycle)-COO-aryl, N(aryl)-CO—NH—(C$_1$-C$_6$)-alkyl), N(heterocycle)-CO—NH—(C$_1$-C$_6$)-alkyl), N(aryl)-CO—NH-aryl, N(heterocycle)-CO—NH-aryl, N(aryl)-CO—N—(C$_1$-C$_6$)-alkyl)$_2$, N(heterocycle)-CO—N—(C$_1$-C$_6$)-alkyl)$_2$, N(aryl)-CO—N((C$_1$-C$_6$)-alkyl)-aryl, N(heterocycle)-CO—N((C$_1$-C$_6$)-alkyl)-aryl, N(aryl)-CO—N-(aryl)$_2$, N(heterocycle)-CO—N-(aryl)$_2$, aryl, O—(CH$_2$)$_n$-aryl, O—(CH$_2$)$_n$-heterocycle, where n may be 0-6, where the aryl radical or heterocyclic radical may be substituted one to 3 times by F, Cl, Br, I, OH, CF$_3$, NO$_2$, CN, OCF$_3$, O—(C$_1$-C$_6$)-alkyl, (C$_1$-C$_6$)-alkyl, NH$_2$NH(C$_1$-C$_6$)-alkyl, N((C$_1$-C$_6$)-alkyl)$_2$, SO$_2$—CH$_3$, COOH, COO—(C$_1$-C$_6$)-alkyl, CONH$_2$.

As used herein, the following definitions apply:

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The amount of a compound of formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of bodyweight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, capsules or tablets, may contain, for example, from 1.0 to 1000 mg, typically from 10 to 600 mg. For the therapy of the above-mentioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of formula (I) may also be administered in combination with other active ingredients.

Further active ingredients suitable for combination products are:

all antidiabetics mentioned in the Rote Liste 2003, chapter 12. They may be combined with the compounds of the formula I of the invention in particular for a synergistic improvement of the effect. Administration of the active ingredient combination may take place either by separate administration of the active ingredients to the patient or in the form of combination products in which a plurality of active ingredients are present in one pharmaceutical preparation. Most of the active ingredients listed below are disclosed in the USP Dictionary of USAN and International Drug Names, US Pharmacopeia, Rockville 2001.

Antidiabetics include insulin and insulin derivatives such as, for example, Lantus® (see www.lantus.com) or HMR 1964, fast-acting insulins (see U.S. Pat. No. 6,221,633), GLP-1 derivatives such as, for example, those disclosed in WO 97/26265, WO 99/03861, WO 01/04156, WO 00/34331, WO 00/34332, WO 91/11457 and U.S. Pat. No. 6,380,357 and orally effective hypoglycemic active ingredients.

The orally effective hypoglycemic active ingredients include, preferably, sulfonylureas, biguanides, meglitinides, oxadiazolidinediones, thiazolidinediones, glucosidase inhibitors, glucagon antagonists, GLP-1 agonists, potassium channel openers such as, for example, those disclosed in WO 97/26265 and WO 99/03861 of Novo Nordisk A/S, insulin sensitizers, inhibitors of liver enzymes involved in the stimulation of gluconeogenesis and/or glycogenolysis, modulators of glucose uptake, compounds which alter lipid metabolism, such as antihyperlipidemic active ingredients and antilipidemic active ingredients, compounds which reduce food intake, PPAR and PXR agonists and active ingredients which act on the ATP-dependent potassium channel of the beta cells.

In one embodiment of the invention, the compounds of the formula I are administered in combination with an HMGCoA reductase inhibitor such as simvastatin, fluvastatin, pravastatin, lovastatin, atorvastatin, cerivastatin, rosuvastatin.

In one embodiment of the invention, the compounds of the formula I are administered in combination with a cholesterol absorption inhibitor such as, for example, ezetimibe, tiqueside, pamaqueside.

In one embodiment of the invention, the compounds of the formula I are administered in combination with a PPAR gamma agonist, such as, for example, rosiglitazone, pioglitazone, JTT-501, Gl 262570.

In one embodiment of the invention, the compounds of the formula I are administered in combination with a PPAR alpha agonist, such as, for example, GW 9578, GW 7647.

In one embodiment of the invention, the compounds of the formula I are administered in combination with a mixed PPAR alpha/gamma agonist, such as, for example, GW 1536, AVE 8042, AVE 8134, AVE 0847, or as described in PCT/US 00/11833, PCT/US 00/11490, DE10142734.4.

In one embodiment of the invention, the compounds of the formula I are administered in combination with a fibrate such as, for example, fenofibrate, clofibrate, bezafibrate.

In one embodiment of the invention, the compounds of the formula I are administered in combination with an MTP inhibitor such as, for example, implitapide, BMS-201038, R-103757.

In one embodiment of the invention, the compounds of the formula I are administered in combination with bile acid absorption inhibitor (see, for example, U.S. Pat. No. 6,245,744 or U.S. Pat. No. 6,221,897), such as, for example, HMR 1741.

In one embodiment of the invention, the compounds of the formula I are administered in combination with a CETP inhibitor, such as, for example, JTT-705.

In one embodiment of the invention, the compounds of the formula I are administered in combination with a polymeric bile acid adsorbent such as, for example, cholestyramine, colesevelam.

In one embodiment of the invention, the compounds of the formula I are administered in combination with an LDL receptor inducer (see U.S. Pat. No. 6,342,512), such as, for example, HMR1171, HMR1586.

In one embodiment of the invention, the compounds of the formula I are administered in combination with an ACAT inhibitor, such as, for example, avasimibe.

In one embodiment of the invention, the compounds of the formula I are administered in combination with an antioxidant, such as, for example, OPC-14117.

In one embodiment of the invention, the compounds of the formula I are administered in combination with a lipoprotein lipase inhibitor, such as, for example, NO-1886.

In one embodiment of the invention, the compounds of the formula I are administered in combination with an ATP-citrate lyase inhibitor, such as, for example, SB-204990.

In one embodiment of the invention, the compounds of the formula I are administered in combination with a squalene synthetase inhibitor, such as, for example, BMS-188494.

In one embodiment of the invention, the compounds of the formula I are administered in combination with a lipoprotein(a) antagonist, such as, for example, CI-1027 or nicotinic acid.

In one embodiment of the invention, the compounds of the formula I are administered in combination with a lipase inhibitor, such as, for example, orlistat.

In one embodiment of the invention, the compounds of the formula I are administered in combination with insulin.

In one embodiment, the compounds of the formula I are administered in combination with a sulfonylurea such as, for example, tolbutamide, glibenclamide, glipizide or glimepiride.

In one embodiment, the compounds of the formula I are administered in combination with a biguanide, such as, for example, metformin.

In one further embodiment, the compounds of the formula I are administered in combination with a meglitinide, such as, for example, repaglinide.

In one embodiment, the compounds of the formula I are administered in combination with a thiazolidinedione, such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, the compounds of the formula I are administered in combination with an α-glucosidase inhibitor, such as, for example, miglitol or acarbose.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with more than one of the aforementioned compounds, e.g. in combination with a sulfonylurea and metformin, with a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., in: Hormone and Metabolic Research (2001), 33(9), 554-558), NPY antagonists, e.g. naphthalene-1-sulfonic acid {4-[(4-aminoquinazolin-2-ylamino)methyl]-cyclohexylmethyl}amide; hydrochloride (CGP 71683A)), MC4 agonists (e.g. 1-amino-1,2,3,4-tetrahydronaphthalene-2-carboxylic acid [2-(3a-benzyl-2-methyl-3 -oxo-2,3,3a,4,6,7-hexahydropyrazolo[4,3-c]pyridin-5-yl)-1-(4-chlorophenyl)-2-oxoethyl]-amide; (WO 01/91752)), orexin antagonists (e.g. 1-(2-methylbenzoxazol-6-yl)-3-[1,5]naphthyridin-4-yl-urea; hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylaamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]-ethanol; hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)); serotonin reuptake inhibitors (e.g. dexfenfluramine), mixed serotoninergic and noradrenergic compounds (e.g. WO 00/71549), 5HT agonists, e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the other active ingredient is dexamphetamine or amphetamine.

In one embodiment, the other active ingredient is fenfluramine or dexfenfluramine.

In another embodiment, the other active ingredient is sibutramine.

In one embodiment, the other active ingredient is orlistat.

In one embodiment, the other active ingredient is mazindol or phentermine.

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6.) Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

It will be appreciated that every suitable combination of the compounds of the invention with one or more of the aforementioned compounds and optionally one or more other pharmacologically active substances is regarded as falling within the protection conferred by the present invention.

The citation of any reference herein should not be construed as an admission that such reference is available as "Prior Art" to the instant application.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

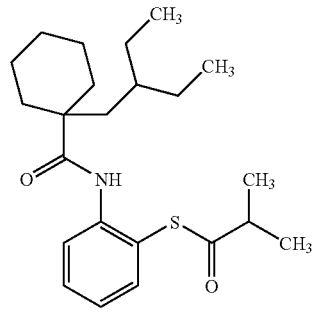

JTT-705

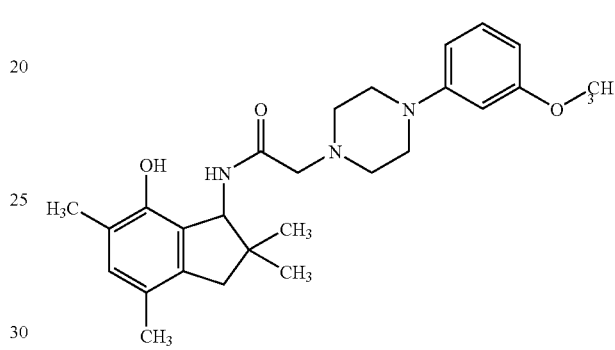

OPC-14117

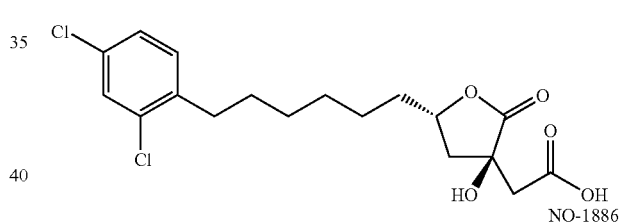

SB-204990

NO-1886

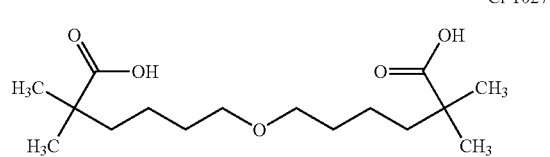

Cl-1027

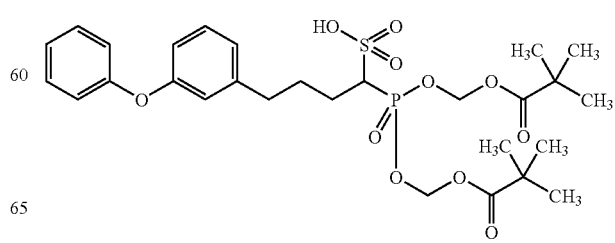

BMS-188494

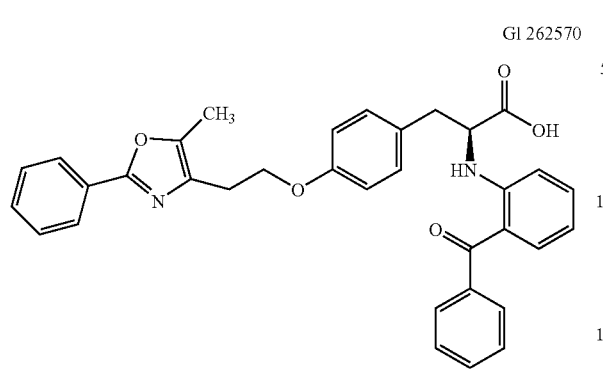
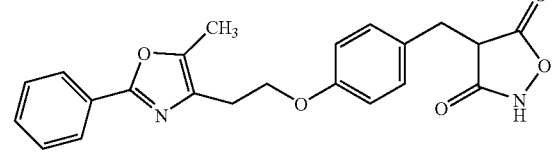
The examples detailed below serve to illustrate the invention but without restricting it. The measured solidification and decomposition points (Fp.) have not been corrected and generally depend on the heating rate.
| Ex. | Structure | Fp. [° C.] |
|---|---|---|
| 1 | 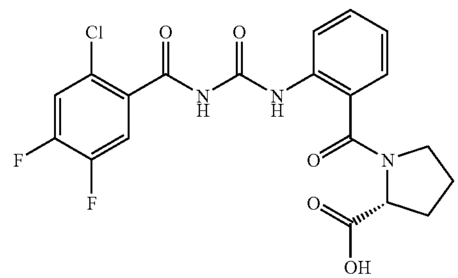 | 123.5 |
| 2 | 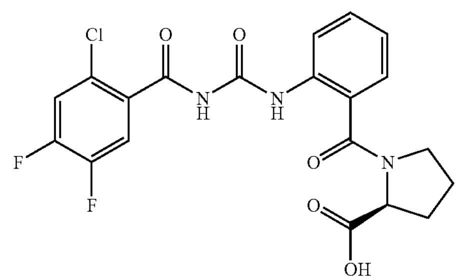 | 128.4 |
| 3 | 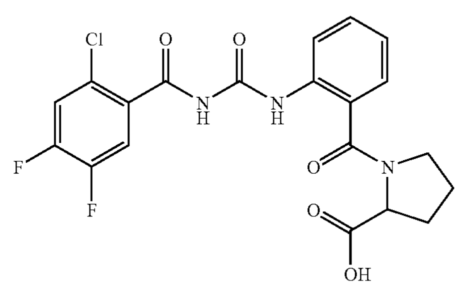 | 193.1 |

-continued

| Ex. | Structure | Fp. [° C.] |
|---|---|---|
| 4 | (structure) | oil |
| 5 | (structure) | 99 (softening) |
| 6 | (structure) | 102 (softening) |
| 7 | (structure) | 125 (softening) |

The activity of the compounds was assayed as follows:

Glycogen Phosphorylase a Activity Assay

The effect of compounds on the activity of the active form of glycogen phosphorylase (GPa) was measured in the reverse direction by following the synthesis of glycogen from glucose 1-phosphate by determining the liberation of inorganic phosphate. All the reactions were carried out as duplicate determinations in microtiter plates with 96 wells (Half Area Plates, Costar No 3696), measuring the change in absorption owing to the formation of the reaction product at the wavelength specified hereinafter in a Multiskan Ascent Elisa Reader (Lab Systems, Finland).

In order to measure the GPa enzymic activity in the reverse direction, the general method of Engers et al. (Engers H D, Shechosky S, Madsen N B, Can J Biochem 1970 July;48(7):746-754) was used to measure the conversion of glucose 1-phosphate into glycogen and inorganic phosphate, with the following modifications: human glycogen phosphorylase a (for example with 0.76 mg of protein/ml (Aventis Pharma Deutschland GmbH), dissolved in buffer solution E (25 mM β-glycerophosphate, pH 7.0, 1 mM EDTA and 1 mM dithiothreitol) was diluted with buffer T (50 mM Hepes, pH 7.0, 100 mM KCl, 2.5 mM EDTA, 2.5 mM $MgCl_2.6H_2O$) and addition of 5 mg/ml glycogen to a concentration of 10 μg of protein/ml. Test substances were prepared as 10 mM solution in DMSO and diluted to 50 μM with buffer solution T. To 10 μl of this solution were added 10 μl of 37.5 mM glucose, dissolved in buffer solution T, and 5 mg/ml glycogen, plus 10 μt of a solution of human glycogen phosphorylase a (10 μg of protein/ml) and 20 μl of glucose 1-phosphate, 2,5 mM. The baseline glycogen phosphorylase a activity in the absence of test substance was determined by adding 10 μl of buffer solution T (0.1% DMSO). The mixture was incubated at room temperature for 40 minutes, and the liberated organic phosphate was measured by the general method of Drueckes et al. (Drueckes P, Schinzel R, Palm D, *Anal Biochem* 1995 Sep. 1;230(1):173-177) with the following modifications: 50 μl of a stop solution of 7.3 mM ammonium molybdate, 10.9 mM zinc acetate, 3.6% ascorbic acid, 0.9% SDS are added to 50 μl of the enzyme mixture. After incubation at 45° C. for 60 minutes, the absorption at 820 nm was measured. To determine the background absorption, in a separate mixture the stop solution was added immediately after addition of the glucose 1-phosphate solution.

This test was carried out with a concentration of 10 μM of the test substance in order to determine the particular inhibition of glycogen phosphorylase a in vitro by the test substance.

TABLE 2

| Biological activity | |
|---|---|
| Ex. | IC-50 (μM) |
| 1 | 0.03 |
| 2 | 2.1 |
| 3 | 0.12 |
| 4 | 0.57 |
| 5 | 0.03 |
| 6 | 1.4 |
| 7 | 4.0 |

It is evident from the table that the compounds of the formula I inhibit the activity of glycogen phosphorylase a and thus are very suitable for lowering the blood glucose levels. They are therefore particularly suitable for the treatment of type I and II diabetes, of insulin resistance, of dyslipidemias, of metabolic syndrome/syndrome X, of pathological obesity and for weight reduction in mammals.

Compounds of the formula I are also suitable, because of their inhibition of PTP1B, for the treatment of hyperglycerimia, high blood pressure, atherosclerosis, dysfunctions of the immune system, autoimmune diseases, allergic diseases such as, for example, asthma, arthritis, osteoarthritis, osteoporosis, proliferation disorders such as cancer and psoriasis, diseases with reduced or increased production of growth factors, hormones or cytokines which induce the release of growth hormones.

The compounds are also suitable for the treatment of nervous system disorders such as, for example, Alzheimer's or multiple sclerosis.

The compounds are also suitable for the treatment of disorders of wellbeing and other psychiatric indications such as, for example, depressions, anxiety states, anxiety neuroses, schizophrenia, for the treatment of disorders associated with the circadian rhythm and for the treatment of drug abuse.

They are additionally suitable for the treatment of sleep disorders, sleep apnea, female and male sexual disorders, inflammations, acne, pigmentation of the skin, disorders of steroid metabolism, skin diseases and mycoses.

The preparation of an example is described in detail below, and the other compounds of the formula I were obtained analogously:

Experimental Part:

EXAMPLE 1

R-1-{2-[3-(2-Chloro-4,5-difluorobenzoyl)ureido] benzoyl}pyrrolidine-2-carboxylic acid 0.148 g of D-proline and 0.2 ml of triethylarnine are added to a solution of 0.2 g of isatoic anhydride in 5 ml of acetonitrile, and the mixture is stirred at room temperature for 2 hours. Then 1.3 mmol of solution of 2-chloro-4,5-difluoro-benzoyl isocyanate in acetonitrile are added dropwise, and the mixture is stirred at room temperature for 30 minutes. After the volatile fractions have been stripped off in vacuo at 40° C., the residue is stirred with 1N hydrochloric acid for 15 hours, and the precipitate which has formed is filtered off with suction and dried in vacuo. Yield: 0.61 g Fp.: 123.5° C.

The further examples were prepared analogously.

The invention claimed is:

1. A compound of the formula I,

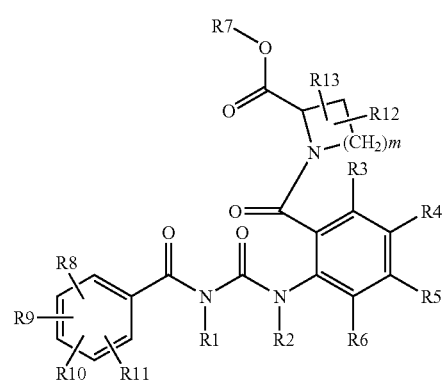

wherein

R1, R2 are H;

R3, R4, R5, R6 are H;

R7 is H or ($C_1$-$C_6$)-alkyl;

R8, R9 are each, independently of one another, F or Cl;

R10, R11 are each, independently of one another, H, F, or Cl;

R12, R13 are each, independently of one another, H or F; or

R12 and R13 form together, with the carbon atom or the carbon atoms to which they are bonded, a 5- or 6-membered, saturated ring;

m is 1, 2, or 3; or and pharmaceutically acceptable salts thereof.

2. A pharmaceutical composition comprising one or more compounds of claim 1 and a pharmaceutically acceptable carrier.

* * * * *